US011045202B2

(12) United States Patent
Amplatz et al.

(10) Patent No.: US 11,045,202 B2
(45) Date of Patent: Jun. 29, 2021

(54) FLANGED OCCLUSION DEVICES AND METHODS

(71) Applicant: St. Jude Medical, Cardiology Division, Inc., St. Paul, MN (US)

(72) Inventors: Kurt Amplatz, North Oaks, MN (US); Gary A. Thill, Vadnais Heights, MN (US); Pat Russo, Vadnais Heights, MN (US); Xiaoping Gu, Maplewood, MN (US); Jana Santer, Spring Lake Park, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 212 days.

(21) Appl. No.: 16/276,245

(22) Filed: Feb. 14, 2019

(65) Prior Publication Data
US 2019/0175185 A1    Jun. 13, 2019

Related U.S. Application Data

(63) Continuation of application No. 15/271,746, filed on Sep. 21, 2016, now Pat. No. 10,231,737, which is a
(Continued)

(51) Int. Cl.
*A61B 17/12*    (2006.01)
*A61B 17/00*    (2006.01)

(52) U.S. Cl.
CPC .... *A61B 17/12022* (2013.01); *A61B 17/0057* (2013.01); *A61B 17/12122* (2013.01);
(Continued)

(58) Field of Classification Search
CPC .......... A61B 2017/00632; A61B 2017/00615; A61B 2017/00592; A61B 2017/00575;
(Continued)

(56) References Cited

U.S. PATENT DOCUMENTS

| 4,055,233 A | 10/1977 | Huntress |
| 4,564,009 A | 1/1986 | Brinkoff |

(Continued)

FOREIGN PATENT DOCUMENTS

| CA | 2252913 A1 | 6/2002 |
| CA | 2302164 A1 | 3/2004 |

(Continued)

OTHER PUBLICATIONS

Meier, Berhard et al. "Transcatheter Left Atrial Appendage Occlusion with Amplatzer Devices to Obviate Anticoagulation in Patients with Atrail Fibrillation", Catheterization and Cardiovascular Interventations 60:417-422 (2003).
(Continued)

*Primary Examiner* — Jocelin C Tanner
(74) *Attorney, Agent, or Firm* — Armstrong Teasdale LLP

(57) ABSTRACT

Implantable occlusion devices that include one or more flanges extending from a tubular body are disclosed. The flange or flanges may assist in retention of the device within a vessel, cavity, appendage, etc. At least one flange on the occlusion device may include a concave surface proximate one end of a body. Because of the shape of the flange, e.g., its concavity, the occlusion device may resist dislocation due to e.g., the forces generated within the left atrial appendage during atrial fibrillation.

13 Claims, 2 Drawing Sheets

Related U.S. Application Data continuation of application No. 11/476,947, filed on Jun. 27, 2006, now Pat. No. 9,743,932, which is a continuation of application No. PCT/US2005/010551, filed on Mar. 31, 2005.

(60) Provisional application No. 60/560,825, filed on Apr. 8, 2004.

(52) U.S. Cl.
CPC .............. *A61B 17/12172* (2013.01); *A61B 2017/00243* (2013.01); *A61B 2017/00575* (2013.01); *A61B 2017/00592* (2013.01); *A61B 2017/00615* (2013.01); *A61B 2017/00632* (2013.01)

(58) Field of Classification Search
CPC .......... A61B 2017/00243; A61B 2017/00606; A61B 17/12172; A61B 17/12122; A61B 17/12022; A61B 17/0057
See application file for complete search history.

(56) References Cited

U.S. PATENT DOCUMENTS

| | | | |
|---|---|---|---|
| 5,522,822 A | | 6/1996 | Phelps et al. |
| 5,683,411 A | | 11/1997 | Kavteladze et al. |
| 5,723,005 A | | 3/1998 | Herrick |
| 5,725,552 A | | 3/1998 | Kotuula et al. |
| 5,846,261 A | * | 12/1998 | Kotula ................ A61F 2/01 606/213 |
| 5,861,003 A | * | 1/1999 | Latson ............... A61B 17/0057 606/157 |
| 5,944,738 A | * | 8/1999 | Amplatz ............ A61B 17/0057 606/213 |
| 6,027,470 A | | 2/2000 | Mendius |
| 6,123,715 A | | 9/2000 | Amplatz et al. |
| 6,168,622 B1 | | 1/2001 | Mazzocchi |
| 6,234,175 B1 | | 5/2001 | Zhou et al. |
| 6,369,339 B1 | | 4/2002 | Amplatz |
| 6,447,531 B1 | | 9/2002 | Amplatz |
| 6,468,303 B1 | * | 10/2002 | Amplatz ................ A61B 17/11 623/1.2 |
| 6,551,303 B1 | | 4/2003 | Van Tassel et al. |
| 6,579,303 B2 | | 6/2003 | Amplatz |
| 6,599,308 B2 | | 7/2003 | Amplatz |
| 6,830,124 B2 | | 12/2004 | Chiang |
| 7,025,776 B1 | | 4/2006 | Houser et al. |
| 2001/0000767 A1 | | 5/2001 | Ezawa et al. |
| 2003/0195553 A1 | * | 10/2003 | Wallace ........... A61B 17/12172 606/200 |
| 2003/0220667 A1 | | 11/2003 | Van Der Burg et al. |
| 2005/0228434 A1 | * | 10/2005 | Amplatz .......... A61B 17/12109 606/200 |

FOREIGN PATENT DOCUMENTS

| | | |
|---|---|---|
| CA | 2402101 A1 | 1/2007 |
| EP | 2856949 B1 | 10/2015 |
| GB | 2020557 A | 11/1979 |
| JP | H0447415 U | 4/1992 |
| WO | 96/01599 A1 | 1/1996 |
| WO | 97/42878 A1 | 11/1997 |
| WO | 99/12478 A1 | 3/1999 |
| WO | 99/39646 A1 | 8/1999 |
| WO | 01/72367 A1 | 4/2001 |
| WO | 02071977 A2 | 9/2002 |
| WO | 02098282 A2 | 12/2002 |
| WO | 2004064671 A2 | 8/2004 |
| WO | 2005099365 A2 | 10/2005 |

OTHER PUBLICATIONS

European Search Report for Application No. 13173875.9-1506 dated Aug. 26, 2013; 5 pages.

\* cited by examiner

FLANGED OCCLUSION DEVICES AND METHODS

CROSS-REFERENCE TO RELATED APPLICATIONS

This application is a continuation application of U.S. patent application Ser. No. 15/271,746, filed on Sep. 21, 2016, which is a continuation application of U.S. patent application Ser. No. 11/476,947, filed on Jun. 27, 2006, which is a continuation of prior PCT Application PCT/US2005/010551 filed on Mar. 31, 2005, and claims priority to U.S. Patent Application No. 60/560,825, filed on Apr. 8, 2004, the entire contents and disclosures of which are hereby incorporated herein by reference in their entireties.

The present invention relates to the field of implantable medical devices, more particularly to implantable medical devices designed to occlude vessels, cavities, appendages, etc. within a body.

A variety of devices and/or techniques have been developed to occlude a vessel or an opening in an organ (e.g., heart) of a patient. U.S. Pat. No. 5,725,552 (Kotula et al.); U.S. Pat. No. 5,846,261 (Kotula et al.); U.S. Pat. No. 5,944,738 (Amplatz et al.); U.S. Pat. No. 6,123,715 (Amplatz et al.); U.S. Pat. No. 6,368,339 B1 (Amplatz); U.S. Pat. No. 6,447,531 B1 (Amplatz); U.S. Pat. No. 6,579,303 B2 (Amplatz); U.S. Pat. No. 6,599,308 (Amplatz), etc. describe a variety of different devices that may be capable of achieving the desired occlusion (along with materials for and methods of manufacturing such devices).

The devices described in the above-identified patents may not, however, be well-suited to address physiological conditions such as, e.g., occlusion of the left atrial appendage (LAA) to reduce the risk of embolisms when the left atrial appendage is undergoing atrial fibrillation. Atrial fibrillation in the left atrial appendage may be a significant factor in the formation of embolisms. Occlusion of the left atrial appendage by surgical techniques, while possible, is not always possible and/or advisable. Furthermore, although some of the devices described in the above-identified patents may be used to occlude the left atrial appendage, they may be undesirably expelled from the left atrial appendage due to, e.g., forces generated by atrial fibrillation.

SUMMARY OF THE INVENTION

The present invention provides implantable occlusion devices that include one or more flanges extending from a tubular body. The flange or flanges may assist in retention of the device within a vessel, cavity, appendage, etc.

It may be preferred that at least one flange on the occlusion device include a concave surface proximate one end of a body. The shape of the flange, e.g., its concavity, may help the occlusion device to resist dislocation due to, e.g., the forces generated within the left atrial appendage during atrial fibrillation. In other embodiments, the location of the flange lip, e.g., between the opposing axial ends of the body of the occlusion device may assist the device in resisting dislocation due to forces generated within the left atrial appendage during atrial fibrillation. In still other embodiments, multiple flanges with concave outer surfaces as described herein may also assist in retaining the occlusion device in a selected location.

The flange or flanges on occlusion devices according to the present invention may also preferably have a convex outer surface facing away from the body of the device. If such a convex outer surface and a concave outer surface facing the body are used to form the flange, the result flange lip and shape of the flange may be particularly capable of resisting dislocation from the left atrial appendage during atrial fibrillation.

As used herein, an "outer surface" of an occlusion device of the present invention is a surface that faces outward from the interior of the device. An outer surface will typically be defined by the material used to manufacture the devices and use of the term "surface" does not require that the surface be solid. In connection with the invention, for example, a porous material (such as, e.g., braided strands) may define an outer surface while still including openings between the strands.

As with the occlusion devices described in the patents identified above, it may be preferred that the occlusion devices of the present invention be manufactured of porous materials. It may be preferred, for example, that the materials used to form the occlusion devices of the present invention have pore sizes of 100 micrometers or less. It may be preferred that the occlusion devices be manufactured from strands that are (preferably) braided, woven, knitted, etc., such that after implantation, the devices may preferably collect thrombi on the surfaces of the device, eventually permitting the device to occlude the left atrial appendage.

The patents identified herein also describe a number of potentially suitable methods of manufacturing the occlusion devices of the present invention. It may be preferred for example, that the materials and methods used to manufacture the occlusion devices of the present invention provide devices that can be compressed for delivery to an internal body location and that will expand spontaneously and/or under the application of heat (or another initiator) that causes the devices to expand into their relaxed configuration. As a result, it may be preferred that the occlusion devices be manufacture of resilient materials capable of compression and expansion as described herein. Examples of some potentially suitable materials may include, e.g., shape memory materials such as, e.g., nickel titanium alloys, etc.

If the occlusion devices are manufactured by a braided tubular structure, the pick of the fabric forming the devices may preferably be increased from those described in connection with the devices described in the patents identified herein. "Pick" is defined as the number of turns per unit length for braided tubular structures. For example, it may be preferred that the pick be as high as 144 per lineal inch (approximately 55 per centimeter) or higher. Alternatively, the pick may be lower if so desired. In some embodiments, it may be preferred to incorporate a fabric or other structure within or on the occlusion devices (if, e.g., a lower pick is used) to enhance the ability of the occlusion device to collect thrombi and provide the occlusive properties desired.

Deployment of the occlusion devices of the present invention may preferably be accomplished according to the methods described in the patents identified herein preferably using, e.g., catheters and other devices to assist in deployment. It may be preferred, but not required, that the deployment be performed using percutaneous techniques. If so delivered, it may be preferred that the occlusion devices be manufactured of materials that provide a resilient device, capable of collapsing into a collapsed configuration for delivery, but expanding (preferably spontaneously and/or under the application of, e.g., heat) into a relaxed, expanded configuration when deployed at a selected location. Such properties are similar to the devices described in many of the patents identified herein.

In one aspect, the present invention provides a medical device for deployment in a body, wherein the device includes a tubular body with a first end and a second end, wherein the body defines a longitudinal axis extending between the first end and the second end; and wherein the body has a body width measured transverse to the longitudinal axis when the device is in a relaxed configuration; and a flange attached to the body proximate the second end of the body, the flange including a concave outer surface facing the first end of the body and a flange width transverse to the longitudinal axis when the device is in a relaxed configuration. When the device is in the relaxed configuration, the body width proximate the flange is half or more of the flange width.

In another aspect, the present invention provides a medical device for deployment in a body, wherein the device includes a tubular body with a first end and a second end, wherein the body has a longitudinal axis extending between the first end and the second end; and wherein the body has a body width measured transverse to the longitudinal axis when the device is in a relaxed configuration; and a plurality of flanges attached to the body proximate the second end of the body, wherein each flange of the plurality of flanges includes a concave outer surface facing the first end of the body and a flange width transverse to the longitudinal axis when the device is in the relaxed configuration, and wherein the body width proximate each flange of the plurality of flanges is less than the flange width.

In another aspect, the present invention provides a medical device for deployment in a body, wherein the device includes a tubular body with a first end and a second end, wherein the body has a longitudinal axis extending between the first end and the second end; and wherein the body has a body width measured transverse to the longitudinal axis when the device is in a relaxed configuration; and only one flange attached to the body, the only one flange attached proximate the second end of the body, the only one flange having a concave outer surface facing the first end of the body and a flange width transverse to the longitudinal axis when the device is in the relaxed configuration, and wherein the body width proximate the only one flange is less than the flange width.

In another aspect, the present invention provides a method of treating a physiological condition by deploying an occlusion device according to the present invention within the left atrial appendage of a heart.

In some embodiments, the present invention may provide a medical device for deployment in a body, the device including an expanded configuration and a collapsed configuration enabling passage of the device through a lumen of a catheter. The device may include a plurality of strands treated to conform in shape to the expanded configuration of the device, wherein each strand of the plurality of strands has a proximal end and a distal end, wherein at least one of the proximal ends and the distal ends of the plurality of strands are secured at a common endpoint. The device may further include a tubular body formed by the plurality of strands, the tubular body having a first end and a second end, wherein the body defines a longitudinal axis extending between the first end and the second end and a body width measured transverse to the longitudinal axis; and one or more flanges formed by the plurality of strands, the flanges attached to the body proximate the second end of the body, wherein the flanges define a concave surface facing the first end of the body when the device is in the expanded configuration, and wherein the flanges have a flange width transverse to the longitudinal axis that is greater than the body width when the device is in the expanded configuration. Optionally, the flanges define a convex surface facing away from the first end of the body when the device is in the expanded configuration. Optionally, the flanges include a flange lip located distal from the longitudinal axis, and wherein the flange lip is located between the first end and the second end of the body when the device is in the expanded configuration.

In another embodiment, the present invention may provide a medical device for deployment in a body, the device having an expanded configuration and a collapsed configuration enabling passage of the device through a lumen of a catheter. The medical device may include a plurality of strands treated to conform in shape to the expanded configuration of the device, wherein each strand of the plurality of strands has a proximal end and a distal end, wherein at least one of the proximal ends and the distal ends of the plurality of strands are secured at a common endpoint. The device may further include a tubular body formed by the plurality of strands, the tubular body having a first end and a second end, wherein the body defines a longitudinal axis extending between the first end and the second end and a body width measured transverse to the longitudinal axis; and one or more flanges formed by the plurality of strands, the flanges attached to the body proximate the second end of the body, wherein the flange includes a flange lip located distal from the longitudinal axis, and wherein the flange lip is located between the first end and the second end of the body when the device is in the expanded configuration, and wherein the flange has a flange width transverse to the longitudinal axis that is greater than the body width when the device is in the expanded configuration. Optionally, the flange lip is located 1 millimeter or more inward of the second end of the body when the device is in the expanded configuration.

These and other features and advantages of the invention may be described below in more detail in connection with some exemplary embodiments of the invention.

BRIEF DESCRIPTIONS OF THE FIGURES

DESCRIPTION OF EXEMPLARY
EMBODIMENTS OF THE INVENTION

In the following detailed description of some exemplary embodiments of the invention, reference is made to the accompanying figures which form a part hereof, and in which are shown, by way of illustration, specific embodiments in which the invention may be practiced. It is to be understood that other embodiments may be utilized and structural changes may be made without departing from the scope of the present invention.

Figure 1:
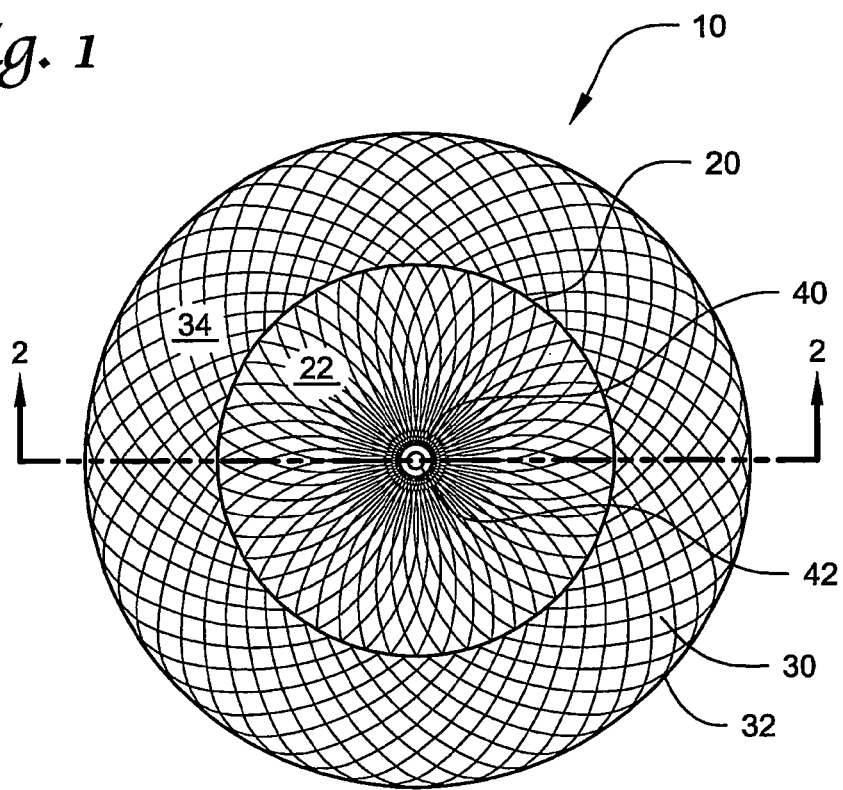
FIG. 1 is a plan view of one exemplary medical device of the present invention.
Figure 2:
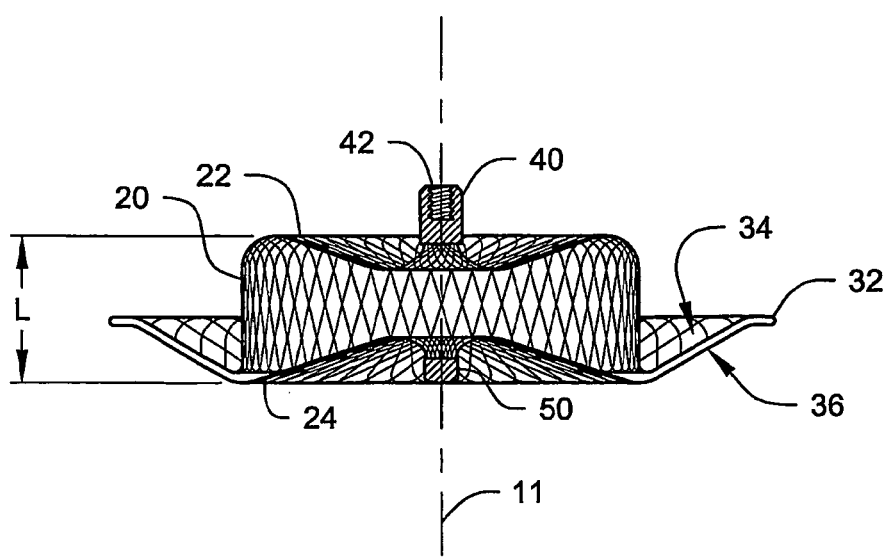
FIG. 2 is a cross-sectional view of the medical device of FIG. 1 taken along line 2-2 in FIG. 1.

FIG. 1 is a plan view of one exemplary medical device according to the present invention (with the view taken along the longitudinal axis seen in FIG. 2) and FIG. 2 is a cross-sectional view of the device 10 taken along line 2-2 in FIG. 2. It may be preferred that the device 10 be constructed of a porous material (such as, e.g., a woven or braided fabric of strands—e.g., metallic strands), such that the device 10 includes openings between its exterior and preferably generally hollow interior volume.

Furthermore, the device 10 is depicted in its expanded or relaxed configuration, i.e., the configuration the device 10 takes when it is not constrained within, e.g., a delivery device, the body of a patient, etc. When collapsed for deployment through, e.g., a catheter or other device, the occlusion device 10 preferably takes a much narrower profile relative to the longitudinal axis 11. That narrow profile may preferably be obtained by, e.g., increasing the distance between the clamps 40 and 50 by drawing the clamps apart under tension.

The device 10 includes a body 20 and a flange 30 attached to the body 20. The body 20 preferably includes a first end or face 22 and a second end or face 24. An imaginary longitudinal axis 11 extends between the first end 22 and the second end of the body 20 (preferably central thereto). The body 20 has a body width measured transverse to and through the longitudinal axis 11. The body width between the first end 22 and the second end 24 may preferably be substantially constant as shown or, alternatively, the body width may vary, e.g., as seen in FIG. 6A of U.S. Pat. No. 6,599,308 B2 (Amplatz). It may be preferred that the maximum body width occur proximate the location at which the flange 30 is connected to the body 20.

It may be preferred that the body 20 be a tubular body. Although the depicted body 20 is in the form of a generally circular tube, it should be understood that the body 20 may alternatively be provided in other tubular shapes, e.g., square, elliptical, oval, hexagonal, or any other suitable tubular shape.

In some embodiments, it may be preferred that the body 20 have a body width at the base of the flange 30, i.e., where the concave surface 34 of the flange 30 meets the body 20, that is half or more of the flange width (where the flange width is also measured between the outer edges of the flange lip 32 in a direction transverse to and through the longitudinal axis 11). In some embodiments, it may be preferred that the body width at the same location be three-fourths or more of the flange width.

Optional clamps 40 and 50 are also depicted in FIGS. 1 & 2 as attached to the body 20. The clamps 40 and 50 may preferably being used to retain the ends of strands used to form the fabric if necessary as described in, e.g., the various patents identified herein. In addition, it may be desirable that at least one of the clamps be adapted to assist in deployment of the device. In the depicted example, clamp 40 may preferably include, e.g., a bore 42 that includes threads such that the device 10 could be rotationally attached to a deployment device that itself includes, e.g., complementary threads. Although the threads are depicted within bore 42, it should be understood that the threads may alternatively be located on the exterior of the clamp 40. Furthermore, many other attachment structures could be used in place of threads to assist in deployment, e.g., grooves, slots, etc.

Although the first end 22 and the second end 24 of the body are depicted as having somewhat concave shapes, it should be understood that either or both the first end 22 and the second end 24 may be provided in any other configuration, e.g., substantially flat, convex, bulbous, etc.

The flange 30 is preferably attached to the body 20 proximate the second end 24 of the body 20. It may be preferred that the flange 30 be preferably formed integrally with the material, e.g., fabric, used to form the body 20 as depicted. As used herein, "integrally" means that the body 20 and the flange 30 are both formed from a single, continuous sheet of, e.g., fabric. Alternatively, it may be possible to form a body 20 and attach a flange 30 to the body 20, with the body 20 and the flange 30 existing as separate and distinct articles before attachment to each other.

The flange 30 may also preferably include a concave surface 34 that preferably faces the first end 22 of the device 10. The concave surface 34 may exhibit curvature in all directions as in, e.g., a parabolic concave surface, or the concave surface may be linear in one or more directions, as in, e.g., an annular ring formed from a section of a conical concave surface. In another variation, the concave surface 34 may be formed from a collection of flat surfaces joined together to approximate a concave surface. In still another variation, portions of the concave surface 34 may be flat and other portions may exhibit curvature. Regardless of the specific shape, it may be preferred that, on the whole, the flange 30 include a concave surface facing towards or opening towards the first end 22 of the body 20.

It may also be preferred that the flange 30 include a convex surface 36 facing away from the first end 22 of the body 20. The convex surface 36 may exhibit curvature in all directions as in, e.g., a parabolic convex surface, or the convex surface 36 may be linear in one or more directions, as in, e.g., an annular ring formed from a section of a conical concave surface. In another variation, the convex surface 36 may be formed from a collection of flat surfaces joined together to approximate a convex surface. In still another variation, portions of the convex surface 36 may be flat and other portions may exhibit curvature. Regardless of the specific shape, it may be preferred that, on the whole, the flange 30 include a convex surface 36 facing away from the first end 22 of the body 20.

The flange 30 preferably includes a flange lip 32 that is preferably located proximate the outermost dimension of the flange width (as measured transverse to the longitudinal axis). The flange lip 32 may preferably form a relatively narrow edge that may assist in retaining the device 10 in location within a patient by deforming the tissue within, e.g., a left atrial appendage. It may be preferred that the concave surface 34 and the convex surface 36 meet at the flange lip 32 as seen in FIG. 2.

In another manner of characterizing the present invention, the flange 30 may be described as preferably including a flange lip 32 that is located between the first end 22 and the second end 24 of the body 20 when the device 10 is in the expanded configuration. In some embodiments, it may be preferred that the flange lip 32 be located 1 millimeter or more inward of the second end 24 of the body 20 (wherein "inward" means towards the first end 22 of the body 20.

In another manner of characterizing the medical devices of the present invention, the medical device 10 may preferably have an axial length ("L" as seen in FIG. 2) measured between the first end 22 and the second end 24 of the body 20 that is less than a maximum width of the flange 30 as measured transverse to the longitudinal axis 11. It may be preferred that the ratio of the axial length to the maximum flange width be 1:1 or less. In other instances, it may be preferred that the same ratio is 0.5:1 or less.

Methods of the present invention may advantageously involve deployment of the medical device in a left atrial appendage of a heart, preferably a human heart. When deployed, it may be preferred that the first end 22 of the body 20 of the medical device 10 faces an interior of the left atrial appendage and that the second end 24 is proximate an opening into the left atrial appendage. If the flange 30 on the medical device 10 includes a concave surface 34 facing the first end 22 of the body 20 of the medical device 10, the concave surface 34 may preferably face the interior of the left atrial appendage. If the flange 30 includes a flange lip 32, the flange lip 32 may preferably be biased against in interior surface of the left atrial appendage. By "biased" it is meant that the forces urging the medical device 10 into its expanded configuration cause the flange lip 32 to exert outward pressure on the interior surfaces of the left atrial appendage.

Figure 3:
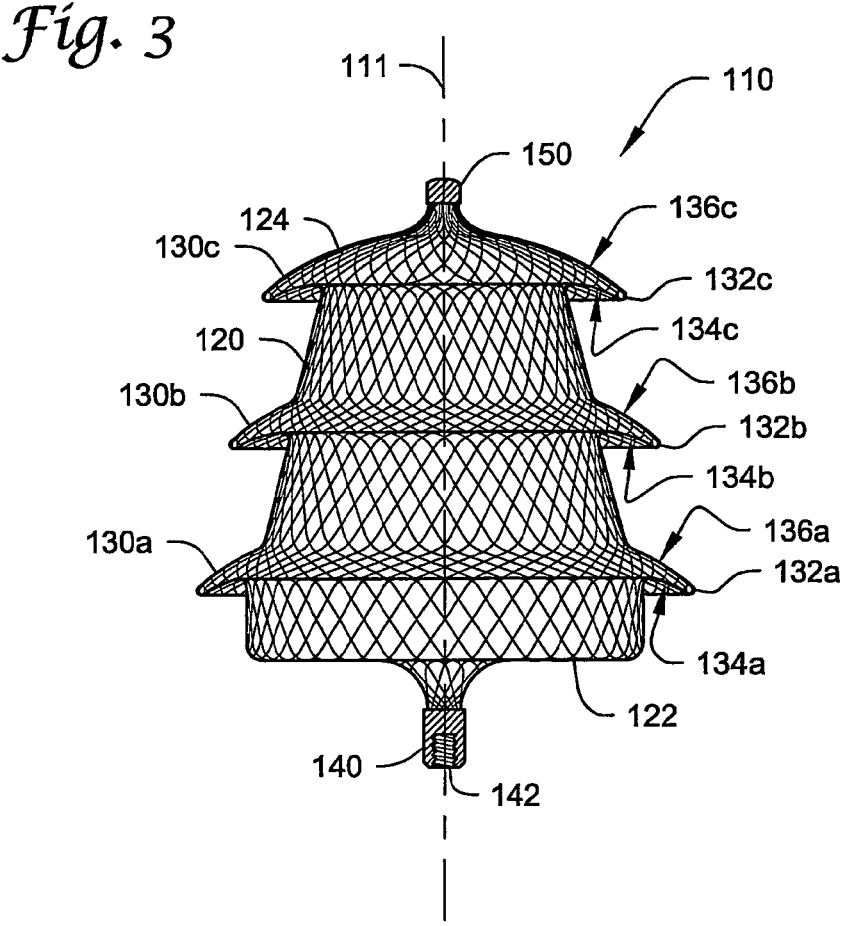
FIG. 3 is a cross-sectional view of an alternative medical device of the present invention.

FIG. 3 depicts another embodiment of an occlusion device according to the present invention in its relaxed or expanded configuration. In some embodiments, it may be preferred that the occlusion devices of the present invention include only one flange as depicted in the device 10 of FIGS. 1 & 2. Alternatively, the occlusion device 110 of FIG. 3 includes a plurality of flanges 130a, 130b, 130c (collectively referred to herein as "flanges 130") extending outwardly from a body 120. Although the depicted occlusion device 110 includes three flanges 130, it should be understood that occlusion devices according to the present invention that include multiple flanges may include as few as two flanges or four or more flanges, with the embodiment depicted in FIG. 3 serving only as an exemplary embodiment of an occlusion device including multiple flanges.

The occlusion device 110 is, with the exception of its size and number of flanges 130, constructed similar to the occlusion device 10 of FIGS. 1 & 2. As such it may preferably be compacted into a collapsed configuration for insertion into the lumen of a delivery device (e.g., catheter, sheath, etc.). When in the collapsed configuration, it may be preferred that the clamps 140 and 150 be located further apart than when the occlusion device 110 is in the relaxed or expanded configuration depicted in FIG. 3.

The variations and optional features described herein with respect to occlusion device 10 apply equally as well to the embodiment depicted in FIG. 3. The occlusion device 110 includes a first end 122, second end 124, clamps 140 and 150 (with clamp 140 preferably including a threaded bore 142), and a (preferably central) longitudinal axis 111. Although depicted as manufactured of braided strands, it could be manufacture of any suitable material.

One feature of the embodiment of FIG. 3 that is not depicted in FIGS. 1 & 2 is the narrowing of the body 120 when moving from the first end 122 to the second end 124 along longitudinal axis 111. As depicted, the body width (as measured transverse to and through the longitudinal axis 111) decreases when moving from the first end 122 to the second end 124. The narrowing in the depicted occlusion device 110 is gradual, resulting in a cone-like shape, but it should be understood that the narrowing is optional (i.e., occlusion devices with multiple flanges need not necessarily include narrowing bodies) and it may take any form (e.g., the narrowing may be stepwise, non-uniform, etc.).

Each the flanges 130 of occlusion device 110 may preferably include a concave surface 134a, 134b, 134c (collectively referred to herein as "concave surfaces 134") that faces the first end 122 of the occlusion device 110. The concave surfaces 134 may exhibit curvature in all directions as in, e.g., a parabolic concave surface, or the concave surfaces may be linear in one or more directions, as in, e.g., an annular ring formed from a section of a conical concave surface. In another variation, each of the concave surfaces 134 may be formed from a collection of flat surfaces joined together to approximate a concave surface. In still another variation, portions of the concave surfaces 134 may be flat and other portions may exhibit curvature. Regardless of the specific shape, it may be preferred that, on the whole, the flanges 130 each include a concave surface 134 facing towards or opening towards the first end 122 of the body 120.

Further, although all of the flanges 130 include a concave surface 134 facing the first end 122 of the body, it should be understood that in embodiments including three or more flanges 130, only two or more of the flanges 130 need include a concave surface 134 facing the first end 122. For example, one of the flanges 130 in the depicted embodiment may be formed without a concave surface facing the first end 122 provided that at least two of the flanges 130 do include a concave surface 134 facing the first end 122.

It may also be preferred that two or more of the flanges 130 include convex surfaces 136a, 136b, 136c ((collectively referred to herein as "convex surfaces 136") facing away from the first end 122 of the body 120. The convex surfaces 136 may exhibit curvature in all directions as in, e.g., a parabolic convex surface, or the convex surfaces 136 may be linear in one or more directions, as in, e.g., an annular ring formed from a section of a conical concave surface. In another variation, the convex surfaces 136 may be formed from a collection of flat surfaces joined together to approximate a convex surface. In still another variation, portions of the convex surfaces 136 may be flat and other portions may exhibit curvature. Regardless of the specific shape, it may be preferred that, on the whole, two or more of the flanges 130 include a convex surface 136 facing away from the first end 122 of the body 120.

Each of the flanges 130 may also preferably include a flange lip 132a, 132b, 132c (collectively referred to herein as "flange lips 132") that is preferably located proximate the outermost dimension of the flange width (as measured transverse to the longitudinal axis). The flange lips 132 may preferably form a relatively narrow edge that may assist in retaining the occlusion device 110 in location within a patient by deforming the tissue within, e.g., a left atrial appendage. It may be preferred that the concave surfaces 134 and the convex surfaces 136 meet at the flange lips 132 as seen in FIG. 3.

Figure 4:
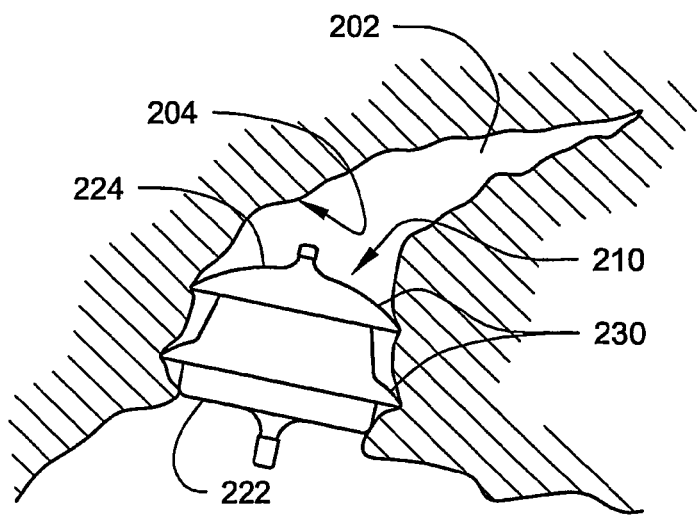
FIG. 4 depicts another occlusion device of the present invention located within a left atrial appendage.

FIG. 4 depicts another exemplary occlusion device 210 of the present invention after placement in a left atrial appendage 202. The occlusion device 210 is depicted in outline form only with flanges 230 biased against the interior surface 204 of the left atrial appendage 202. The first end 222 of the occlusion device 210 faces out of the left atrial appendage 202 while the second end 224 faces into the left atrial appendage. As a result, the concave surfaces of the flanges 230 also face outward, away from the interior of the left atrial appendage 202. As discussed herein, the orientation of the flanges on occlusion devices of the present invention preferably assists their retention in the left atrial appendage 202 after placement. It should be understood that the depicted deployment within a left atrial appendage is exemplary in nature only and the occlusion devices of the present invention may be used in any opening, vessel, cavity etc. where occlusion is desired.

As used herein and in the appended claims, the singular forms "a," "and," and "the" include plural referents unless the context clearly dictates otherwise.

All references and publications identified herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A medical device for deployment in a body, wherein the device comprises:
   a tubular body comprising a first end and a second end, the body defining longitudinal axis extending between the first end and the second end, the body comprising a body width measured transverse to the longitudinal axis; and
   a plurality of flanges attached to the body and extending outwardly from the body and around the entire periphery of the body, wherein each flange of the plurality of flanges respectively comprises a concave outer surface facing the first end of the body and a convex surface facing away from the first end of the body, when the device is in a relaxed configuration,
   wherein, when the device is in the relaxed configuration, the body width proximate each flange of the plurality of flanges is less than the flange width and the body width is greater proximate to the first end of the body than proximate to the second end of the body.

2. A medical device according to claim 1, wherein at least one flange of the plurality of flanges is attached to the body proximate the second end of the body.

3. A medical device according to claim 1, wherein at least one flange of the plurality of flanges comprises a flange lip spaced from the body along a direction transverse to the longitudinal axis, and wherein the flange lip is located between the first end and the second end of the body when the device is in the relaxed configuration.

4. A medical device according to claim 3, wherein the flange lip is configured to be biased against an interior surface of a left atrial appendage.

5. The medical device of claim 3, wherein the concave outer surface and the convex surface of the at least one flange meet proximate the flange lip.

6. The medical device of claim 1, wherein the device comprises a collapsed configuration in which the distance between the first end and the second end is increased such that the body width and the flange width are reduced, enabling passage of the device through a lumen of a catheter, and wherein the device reverts to the relaxed configuration after removal from the lumen.

7. A medical device according to claim 1, wherein the device comprises a plurality of strands treated to conform in shape to the relaxed configuration of the device, wherein each strand of the plurality of strands comprises a proximal end and a distal end, wherein at least one of the proximal ends and the distal ends of the plurality of strands are secured at a common endpoint.

8. A medical device according to claim 7, wherein the plurality of strands are arranged into a fabric.

9. A medical device according to claim 8, wherein the flange comprises two layers of the fabric.

10. A medical device according to claim 7, further comprising a clamp attached to the device at the common endpoint.

11. A medical device according to claim 10, wherein the clamp comprises a thread adapted to rotationally receive a delivery device that comprises complementary threads.

12. A medical device according to claim 1, wherein the body extends proximally towards the first end past a proximal-most flange of the plurality of flanges.

13. A medical device according to claim 12, wherein a maximum body width of the body is measured at a location of the body proximal of the proximal-most flange.

* * * * *